United States Patent
Heesch et al.

(10) Patent No.: US 10,821,244 B2
(45) Date of Patent: Nov. 3, 2020

(54) MEDICAL MEASURING DEVICE, VENTILATOR AND METHOD FOR OPERATING A MEDICAL MEASURING DEVICE OR FOR OPERATING A VENTILATOR

(71) Applicant: Drägerwerk AG & Co. KGaA, Lübeck (DE)

(72) Inventors: Ralf Heesch, Lübeck (DE); Andreas Brandt, Lübeck (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 1332 days.

(21) Appl. No.: 14/904,848

(22) PCT Filed: Jul. 7, 2014

(86) PCT No.: PCT/EP2014/001863
§ 371 (c)(1),
(2) Date: Jan. 13, 2016

(87) PCT Pub. No.: WO2015/007373
PCT Pub. Date: Jan. 22, 2015

(65) Prior Publication Data
US 2016/0136370 A1    May 19, 2016

(30) Foreign Application Priority Data

Jul. 18, 2013    (DE) .................. 10 2013 011 983

(51) Int. Cl.
*A61M 16/00* (2006.01)
*A61B 5/083* (2006.01)

(52) U.S. Cl.
CPC ......... *A61M 16/0069* (2014.02); *A61B 5/083* (2013.01); *A61M 16/0003* (2014.02);
(Continued)

(58) Field of Classification Search
CPC ..... A61M 16/00–0012; A61M 16/0051–0084; A61M 16/0096;
(Continued)

(56) References Cited

U.S. PATENT DOCUMENTS

| 2,904,035 A | 9/1959 | Andreasen |
| 5,400,777 A | 3/1995 | Olsson et al. |

(Continued)

FOREIGN PATENT DOCUMENTS

| CN | 2239820 Y | 11/1996 |
| CN | 1849149 A | 10/2006 |

(Continued)

OTHER PUBLICATIONS

Benjamin et al.: Removal of Bronchial Secretions by Two-Phase Gas-Liquid Transport; Chest 1989;95:658-63; downloaded from http://journal.publications.chestnet.org/.

(Continued)

*Primary Examiner* — Samchuan C Yao
*Assistant Examiner* — Ned T Heffner
(74) *Attorney, Agent, or Firm* — McGlew and Tuttle, P.C.

(57) ABSTRACT

A medical measuring device (2), as well as to a ventilator (1), as well as to a method for operating a medical measuring device (2) or a ventilator are provided. The medical measuring device (1) includes a sensor system (14) and measuring, signal processing and calculating device (21), to detect an inspiratory measured variable, which represents an indicator for the transport of breathing gases into the lungs of a patient (80), and an expiratory measured variable, which represents an indicator for the transport of breathing gases out of the lungs of a patient (80), and to determine an indicator for a ventilation-related shifting of secretion from the expiratory measured variable and the inspiratory measured variable.

24 Claims, 3 Drawing Sheets

(52) U.S. Cl.
CPC ..... *A61M 16/0051* (2013.01); *A61M 16/0066* (2013.01); *A61M 16/0072* (2013.01); *A61M 16/0075* (2013.01); *A61M 2016/003* (2013.01); *A61M 2016/0027* (2013.01); *A61M 2016/0036* (2013.01); *A61M 2016/0039* (2013.01); *A61M 2016/0042* (2013.01); *A61M 2205/3334* (2013.01); *A61M 2205/3584* (2013.01); *A61M 2205/3592* (2013.01); *A61M 2205/502* (2013.01)

(58) Field of Classification Search
CPC ......... A61M 16/04–0402; A61M 16/06–0694; A61M 16/022; A61M 2016/0015–0042; A61M 2016/0413; A61M 2230/00; A61M 2230/005; A61M 2230/202–205; A61M 2230/40–46
See application file for complete search history.

(56) References Cited

U.S. PATENT DOCUMENTS

| | | | |
|---|---|---|---|
| 5,606,968 A | 3/1997 | Mang | |
| 5,937,853 A | 8/1999 | Ström | |
| 6,553,990 B2 | 4/2003 | Hoffmann | |
| 6,571,792 B1 | 6/2003 | Hendrickson et al. | |
| 8,752,546 B2 | 6/2014 | Acker et al. | |
| 2005/0039749 A1 | 4/2005 | Emerson | |
| 2007/0019956 A1 | 8/2007 | Be'eri | |
| 2011/0087123 A9* | 4/2011 | Choncholas | A61M 16/12 600/538 |
| 2011/0220107 A1* | 9/2011 | Kimm | A61M 16/00 128/204.21 |

FOREIGN PATENT DOCUMENTS

| | | |
|---|---|---|
| CN | 102215891 A | 10/2011 |
| DE | 10 2009 003 810 A1 | 10/2009 |
| WO | 2007/023492 A2 | 3/2007 |
| WO | 2007/085110 A1 | 8/2007 |
| WO | 2008/098382 A1 | 8/2008 |
| WO | 2010/022513 A1 | 3/2010 |
| WO | 2010/058308 A2 | 5/2010 |
| WO | 2012/085787 A2 | 6/2012 |
| WO | 2013/068918 A1 | 5/2013 |

OTHER PUBLICATIONS

Volpe et al.: "Ventilation Patterns Influence Airway Secretion Movement": Respiratory Care; Oct. 2008; vol. 53 No. 10.

* cited by examiner

MEDICAL MEASURING DEVICE, VENTILATOR AND METHOD FOR OPERATING A MEDICAL MEASURING DEVICE OR FOR OPERATING A VENTILATOR

CROSS REFERENCE TO RELATED APPLICATIONS

This application is a United States National Phase Application of International Application PCT/EP2014/001863 filed Jul. 7, 2014 and claims the benefit of priority under 35 U.S.C. § 119 of German Patent Application 10 2013 011 983.9 filed Jul. 18, 2013 the entire contents of which are incorporated herein by reference.

FIELD OF THE INVENTION

The present invention pertains to a medical measuring device, a ventilator (also known as a respirator) with a medical measuring device, a method for operating a medical measuring device, as well as a method for operating a ventilator with a medical measuring device.

BACKGROUND OF THE INVENTION

Medical measuring devices are known for the measurement-based testing of medical devices, especially for testing the medical devices for reliable and safe operation during use on a patient.

A ventilator may be defined in this connection, for example, as a ventilator or an anesthesia apparatus. Ventilation of a human being or of a living being can be performed in clinical practice by means of a ventilator. Such a ventilator may be designed as a ventilator for use in an intensive care unit. Such a ventilator may also be an anesthesia apparatus for use in a surgical environment. Such a ventilator may also be designed as an emergency ventilator for use in emergency applications. The breathing air present in the lungs is exchanged cyclically during ventilation in the breathing cycle of a respiration rate. Secretion also takes place in the lungs and in the bronchial tract besides the breathing gases. This secretion, the so-called mucus, which is present in the lungs during spontaneous breathing activity, is removed from the lungs and the bronchial tract, as a rule, by normal, natural exhalation. This removal from the lungs and the bronchial tract is usually supported by additional reactions of a patient, such as coughing or sneezing, which are elicited by stimuli.

During mechanical ventilation by a ventilator, the patient is ventilated, as a rule, by means of an endotracheal tube or a nasal mask. A ventilating tube or a ventilation tube system for an air- and gas-carrying connection to the ventilator is connected to the endotracheal tube or nasal mask. During mechanical ventilation, the breathing of a patient, i.e., the change between inhalation and exhalation, is preset by settings on the ventilator essentially mandatorily, i.e., in a forced and automated manner. The settings of ventilation parameters on the ventilator, such as respiration rate (RR), inspiration time to expiration time ratio (I:E ratio), expiratory pressure and pressure curve, upper flow limits, upper pressure limits, respiratory minute volume (RMV), are usually coupled with ventilation modes. Ventilators according to the state of the art usually allow different forms of "pressure-controlled" and "volume-controlled" ventilation modes. Ventilators for carrying out mechanical ventilation according to the state of the art are described in U.S. Pat. No. 2,904,035, U.S. Pat. No. 5,400,777, U.S. Pat. No. 5,937,853, and WO 2007/085110 A1. Anesthesia apparatuses for performing anesthesia on humans or animals according to the state of the art are described in WO 2008/098382 A1, U.S. Pat. No. 6,571,792 and U.S. Pat. No. 6,553,990.

A method for determining a quality indicator of a ventilation on the basis of an analysis of the work of breathing of a patient is known from WO 2010/022513 A1.

The settings of the ventilator typically affect in this connection not only the gas exchange itself, but possibly also the transport of secretion. An accumulation of secretion in the lungs of a patient may thus occur as well. The general effect of ventilation settings on the transport of secretion is described in the medical clinical literature, such as in Respiratory Care, October 2008, Vol. 53, No. 10. Such accumulation of secretion in the lungs may adversely affect the gas exchange in the lungs and, as a consequence, also the exchange of $CO_2$ and $O_2$ in the blood. This problem is typically solved in clinical practice by the clinical staff performing a so-called secretion suction at regular intervals within the framework of clinical routine. The patient is briefly disconnected from the ventilator for this, i.e., the air- or gas-carrying connection between the ventilator and the patient is interrupted and the secretion is suctioned out of the lungs via the endotracheal tube by means of a secretion suction means.

Such a secretion suction means is shown in U.S. Pat. No. 5,606,968. The usual clinical routine is based essentially on empirical values concerning the frequency of the application of secretion suction and concerning the time intervals between the secretion suctions over the course of the day. In addition, the individual clinical pictures of the patients, as well as the constitution and the age of the latter may also be included in the routine.

The ventilation modes selected and/or the ventilation parameters selected on the ventilator may affect the distribution of secretion in the bronchial tract or the lungs of a patient. Furthermore, the ventilation modes and/or ventilation parameters selected may affect the quantitative distribution of the secretion within the bronchial area (upper bronchial tract, lower bronchial tract, lungs). The wide variety of the interactions between the settings on the ventilator and the personal constitution and the clinical pictures of the different patients may cause the secretion suctions to be performed in clinical routine at time intervals that do not always have to be adapted to the individual requirements of the patients in the clinical practice.

In most cases, the secretion suction situation represents both an uncomfortable, at times painful process, which does, however, always compromise the constitution and the general well-being. In addition, the disconnected patient cannot be briefly ventilated for the duration of suctioning.

SUMMARY OF THE INVENTION

An object of the present invention is to eliminate this and other drawbacks of the state of the art. In particular, a device shall be provided, with which a shifting of secretion into the lungs, especially the lower and deeper areas of the lungs, can be reduced as much as possible.

Furthermore, another object of the present invention is to provide a method for operating a device with reduced shifting of secretion into the lungs, especially into the lower and deeper areas of the lungs.

A device according to the present invention has a sensor system and means for measuring, signal processing and calculation, wherein the sensor system is designed (configured):

to detect an inspiratory measured variable, which represents an indicator for the transport of breathing gases into the lungs of a patient, and wherein the sensor system is designed to detect an expiratory measured variable, which represents an indicator for the transport of breathing gases out of the lungs of a patient, and wherein the means for measuring, signal processing and calculation are designed (configured):

to determine an indicator for a ventilation-related shifting of secretion from the expiratory measured variable and the inspiratory measured variable.

The sensor system is designed to detect an inspiratory measured variable, which represents an indicator for the transport of breathing gases into the lungs of a patient. The sensor system is designed, furthermore, to detect an expiratory measured variable, which represents an indicator for the transport of breathing gases out of the lungs of a patient. The sensor system may comprise in the sense of the present invention a sensor or a plurality of sensors, which are arranged in or connected to the device such as to detect movements of air or gas into the lungs or out of the lungs and to make these available as measured data for the measuring, signal processing and calculation means. The sensor system may preferably comprise one or more flow sensors.

Detection is typically defined in the sense of the present invention as any type of detection of a state variable, a physical, electrical or chemical measured variable or of an electrical signal representing the measured variable in the form of an electric voltage, electric current or electric resistance.

In the sense of the present invention, inspiratory measured variables may be measured variables detected by the sensor system, which are qualitatively and/or quantitatively characteristic of movements of air or gas or of quantities of air or gas into the lungs. In particular, an inspiratory flow rate represents a preferred embodiment of an inspiratory measured variable in the sense of the present invention.

In the sense of the present invention, expiratory measured variables may be measured variables detected by the sensor system, which are qualitatively and/or quantitatively characteristic of movements of air or gas or of quantities of air or gas. In particular, an expiratory flow rate represents a preferred embodiment of an expiratory measured variable in the sense of the present invention.

The measuring, signal processing and calculating means are advantageously designed to detect or record, convert and further process measured values, signals or data of the sensor system or other data sources and/or to carry out conversions with these measured values, signals or data.

The measuring, signal processing and calculating means are preferably designed as a combination or combinations of measuring means, signal processing means and calculating means together in one measuring, signal processing and calculating unit. In an alternative embodiment, the measuring means, signal processing means and calculating means may also be designed as individual assembly units, combinations of individual assembly units or as components of other and/or additional assembly units. The processing, conversion, calculation or conversion of measured values, signals and data is defined in the sense of the present invention as any type of signal matching, signal preamplification, signal amplification, analog or digital filtering, analog to digital conversion, digital to analog conversion, mathematical calculations or conversions. The term sensor system is defined in the sense of the present invention as a conversion of physical or chemical measured signals, such as pressure, pressure difference, partial pressure, temperature, humidity, substance concentration, velocity, flow velocity, flowthrough velocity, flow rate, volume, time into an electric voltage, current or resistance equivalent.

Furthermore, it is also conceivable within the framework of the present invention that elements, parts of the measuring, signal processing and calculating means or unit, such as elements or parts for detection, processing, conversion, for example, voltage measurement, current measurement, resistance measurement, signal matching, signal preamplification, signal amplification, analog or digital filtering, analog to digital conversion, digital to analog conversion, may be integrated in the sensor system besides a sensory element for measuring a physical or chemical measured variable. The measuring, signal processing and calculating means are designed, furthermore, to determine an indicator for a ventilation-related shifting of secretion from the inspiratory measured variable, which represents an indicator for the transport of breathing gases into the lungs of a patient, and from the expiratory measured variable, which represents an indicator for the transport of breathing gases out of the lungs of a patient.

In the sense of the present invention, the indicator for a ventilation-related shifting of secretion may be a value determined, derived, predicted, estimated or calculated from the expiratory measured variable and the inspiratory measured variable, which represents a characteristic, an index, a derived or calculated ratio, a mathematical relationship, or a relation showing in what way a ventilation-related shifting of secretion is present. A variant of the indicator according to the present invention for a ventilation-related shifting of secretion may comprise, for example, the ratio of the inspiratory measured variable to the expiratory measured variable or be derived from this quotient. The ratio of the inspiratory measured variable to the expiratory measured variable can be formed here in a mathematical form from a quotient of a measured value or a sequence of measured values of the inspiratory measured variable to a measured value or a sequence of measured values of the expiratory measured value.

Among other things, the following advantages arise from the present invention for the operation of medical devices, especially ventilators or anesthesia apparatuses. The indicator for a ventilation-related shifting of secretion makes it possible to adapt settings on the ventilator or anesthesia apparatuses for ventilating a patient. This adaptation of the ventilation settings can make it possible to obtain a more comfortable situation for the patient concerning the frequency of secretion suctions and the effort needed for secretion suction. The provision of an indicator for a ventilation-related shifting of secretion by the present invention makes possible a suitable adaptation of the ventilation settings in relation to the distribution of secretion in the bronchial tract and to the accumulation of secretion in the lungs. As a consequence, this may advantageously lead to a reduction of the frequency of secretion suctions, to a minimization of the effort needed in terms of secretion suctions, as well as to a reduction of the number and/or durations of disconnections. On the whole, it is thus possible that there will be a reduced stress on the constitution and the general well-being of a patient thanks to the present invention. Without a support by the indicator for a ventilation-related shifting of secretion, it is often difficult for the user, especially because of the diversity of the possible interactions between ventilation modes, to estimate in what way the ventilation just selected at present facilitates an accumulation of secretion in the lungs, especially in deeper areas of the lungs, or whether it facilitates such secretion to a lesser extent, solely on the basis of displayed measured values or diagrams on the ventilator, for example, from a curve of the ventilation pressure or from the curve of the flow rate.

In a preferred embodiment of the medical measuring device, the measuring, signal processing and calculating means are designed to perform a comparison of the indicator for the ventilation-related shifting of secretion with a defined value. The defined value may be preferably designed as a threshold value. It can be determined by a comparison of the indicator determined before for a ventilation-related shifting of secretion with the defined value or with the threshold value whether an inspiratory impulse, i.e., a transport of secretion into the lungs, or an expiratory impulse, i.e., a transport of secretion out of the lungs, prevails during the performance of the ventilation. If the inspiratory impulse and the expiratory impulse are at an equilibrium with one another, the quotient of the inspiratory impulse and the expiratory impulse mathematically leads to a secretion index value ($S_i$) of 1.0, at which there is, as a rule, no shifting of secretion. The secretion index value ($S_i$) of 1.0 can thus preferably be used as a mean reference and comparison variable for the ventilation-related shifting of secretion and/or as a possible defined value or possible threshold value. The defined value may preferably also be designed as a threshold value range with an upper threshold value and a lower threshold value, so that a hysteresis is obtained between the lower threshold value and the upper threshold value. The range of the hysteresis is also preferably a desired range of the indicator for a ventilation-related shifting of secretion. The definition of the terms defined value or threshold value also covers threshold value ranges in the sense of the present invention, so that comparisons of the indicator for a ventilation-related shifting of secretion with a defined value, for example, a value higher than the upper threshold value as well as a value lower than the lower threshold value, represent a deviation from the desired range of the indicator for a ventilation-related shifting of secretion. A value below the upper threshold value and at the same time a value above the lower threshold value represent, by contrast, a situation in which the indicator for a ventilation-related shifting of secretion is within the desired range. The defined value or threshold value ($S_{Basis}$) is preferably set in the range of 0.8 to 1.2.

If the inspiratory impulse prevails ($S_i>1.0$), the secretion, i.e., the mucus, is transported predominantly in the direction of the lungs into the patient due to the manner in which the ventilation is performed and the ventilation settings causing this. This manner of ventilation thus indirectly leads to the possibility that secretion suctions on the patient must be carried out more often, with a greater effort or over a longer duration in time. If, by contrast, the expiratory impulse prevails ($S_i<1.0$), a transport of the secretion from the direction of the lungs and out of the patient is supported by the manner of ventilation and the ventilation settings causing this, so that it is conceivable that the needed frequency, effort and duration of secretion suctions can be reduced as a consequence. It may be ideally assumed for a recumbent patient that the force of gravity has a negligible effect on the shifting of the secretion in the bronchial space of a patient during a time phase of an inspiration (inspiration phase) and also during a time phase of an expiration (expiration phase). Thus, a target value of $S_i\sim1.0$ represents for a recumbent patient a state in which the expiratory impulse and the inspiratory impulse are at an equilibrium, and the consequence arises from this at the same time that no secretion is shifted or moves in the direction of the lungs of a patient at this value of $S_i\sim1.0$. With the patient in the sitting position, the force of gravity intensifies the shifting of secretion into the lungs of a patient, and a target value of $S_i<1.0$, for example, $S_i\sim0.9$, should therefore be reached in order to ensure that the shifting due to the force of gravity and the ventilation-related shifting of secretion into the lungs of a patient will result, all in all, in an equilibrium of the inspiratory impulse and the expiratory impulse, so that no secretion will be shifted or move as a result in the direction of the lungs of a patient.

Outputting and/or transmission means are arranged in or at the medical measuring device or are connected to the medical measuring device in a preferred embodiment of the medical measuring device. The outputting and/or transmission means are designed to output or transmit data, state or status information. The outputting and/or transmission means are preferably designed together with inputting means, which are preferably present, in an inputting, outputting and transmission unit. The inputting, outputting and transmission unit is preferably designed to output or transmit data, state or status information, and is intended for inputs and for operation by a user.

An output, transmission or forwarding is designed as any form of output, transmission or forwarding of information, measured values, data, state or status information, especially also the output, transmission or forwarding of the indicator according to the present invention for the ventilation-related shifting of secretion. An input or operation is defined in the sense of the present invention as any action or interaction, such as data or value inputs, the initiation and ending of procedures, processes or process steps on the medical measuring device by the user.

An output is defined in the sense of the present invention as any type and manner of an optical, numerical, visual, graphic, pictorial, acoustic output or representation.

The forwarding or transmission of data is defined in the sense of the present invention as any type and manner of a wired or wireless forwarding and transmission to another device, system, computer system, data network, data processing system or output or display system.

In another preferred manner, the measuring, signal processing and calculating means may be designed as a common operation and control module with the inputting, outputting and transmission unit.

The operating and control module may also be provided partially or as a whole as a computer program or as a computer program product, so that the scope of protection of the present application also covers the computer program product and the computer program. In another preferred embodiment, the outputting and/or transmission means, the inputting, outputting and transmission unit or the operating and control module are designed to output, display or transmit the indicator ($S_i$) for a ventilation-related shifting of secretion, a result of the comparison of the indicator for the ventilation-related shifting of secretion with a defined value or an indication concerning a relation of the indicator of the ventilation-related shifting to the defined value.

The indication and the type and manner of the indication concerning a relation of the indicator of the ventilation-related shifting are preferably obtained from a direct mathematical comparison of the secretion index value ($S_i$) with the defined value or threshold value ($S_{Basis}$). The indication may be implemented in the sense of the present invention as any type and manner of an optical, numeric, visual, graphic, pictorial, acoustic output. For example, a type of an indication of a graphic output may thus be implemented in such a form that a display element, for example, an optically active element, a screen element, illuminant or an LED, emits light in a green color in case the expiratory impulse ($S_i<0.9$) prevails, light in a red color in case the inspiratory impulse prevails ($S_i>1.1$), light in an orange color in case the expiratory impulse and the inspiratory impulse are nearly at an equilibrium ($S_i\sim1.0$), in the range of hysteresis ($0.9<S_i<1.1$).

The measuring, signal processing and calculating means are preferably designed to determine the indicator for a ventilation-related shifting of secretion from a quotient of the inspiratory measured variable and the expiratory measured variable. The formation of a quotient from the inspiratory measured variable and the expiratory measured variable makes it advantageously possible to estimate how the ventilation currently being performed affects the ventilation-related shifting of secretion on the basis of an individual indicator.

The sensor system for detecting the inspiratory measured variable is preferably implemented by an inspiratory flow sensor, which is designed to quantitatively determine an inspiratory value of a quantity of gas flowing during inspiration through this inspiratory flow sensor. The sensor system for detecting the expiratory measured variable is preferably implemented by an expiratory flow sensor, which is designed to quantitatively detect an expiratory value of a quantity of gas flowing through this expiratory flow sensor. In another preferred manner, the sensor system for detecting the inspiratory and expiratory measured variables is implemented by an inspiratory and expiratory flow sensor, which is designed to qualitatively detect a direction of a quantity of gas flowing through this inspiratory and expiratory flow sensor and to quantitatively detect a value of the quantity of gas flowing through this inspiratory and expiratory flow sensor. The inspiratory flow sensor and/or the expiratory flow sensor or the inspiratory and expiratory flow sensor are preferably connected to the patient by means of a mouthpiece of a nasal mask or of a connection piece, a so-called Y-piece. An inspiratory and expiratory flow measurement at a measuring site with an inspiratory and expiratory flow sensor offers the advantage that the inspiratory and expiratory measured values were obtained in identical flow states and at identical measurement times, so that there is hardly any inaccuracy due to a time shift in the inspiratory and expiratory measured values in relation to one another. This is a great advantage for the quality and accuracy in the determination of the indicator for the ventilation-related shifting of secretion, especially with the formation of the quotient of the inspiratory measured variable to the expiratory measured variable.

In a likewise preferred manner, the inspiratory and expiratory flow sensor is a flow sensor located close to the patient. It is also preferable for the flow sensor located close to the patient to be arranged in or at the connection piece to the patient, the so-called Y-piece.

A flow sensor located close to the patient at the Y-piece offers the advantage that there are no changes in the state of flow between the state of flow directly close to the patient and the measuring site due to components, for example, ventilation tubes, bacteria filters or water traps, through which flow takes place locally. These additional components usually have a specific effect each on pressure and/or flow conditions, so that the inspiratory and expiratory measured variables may possibly be affected differently as a consequence. If these specific effects cannot be reduced or eliminated by measurement and/or cannot be taken into account in the calculation, this may lead to an adverse effect in the determination of the indicator for the ventilation-related shifting of secretion. This adverse effect can be reduced by the use of the flow sensor located close to the patient at the Y-piece.

Flow sensors according to the state of the art, which are predominantly used in ventilators or anesthesia apparatuses, detect the flow, for example, according to the heat transport method (hot wire anemometer, thermopile, thermistor), the pressure difference method ($\Delta P$), or the ultrasound travel time method. The flow sensors may be arranged in the flow in a centered or central manner in the flow duct, at the edge of the flow duct. Furthermore, an integral measurement (hot wire array in the center of the flow to detect the main stream), or a spot measurement (thermopile array at the edge of the flow duct to detect edge flows or wall shear stresses) of the flow may be performed by the array.

In another preferred manner, the sensor system for detecting the inspiratory measured variable may be implemented by an inspiratory pressure sensor. In another preferred manner, the sensor system for detecting the expiratory measured variable may be implemented by an expiratory pressure sensor.

In another preferred embodiment, the expiratory and inspiratory measured variables are converted in a reference to a time dimension. Such conversions in reference to the time dimension are the formation of an integral ($\int f(t)dt$) according to the time or a formation of a derivation ($dx/dt$) according to the time. For example, it is thus possible to determine an inspiratory or expiratory volume from the measured variables of the flow sensors by means of the integral formation, or an inspiratory or expiratory pressure gradient or a curve of a pressure rise from the measured variables of the pressure sensors by means of differential calculation. The inspiratory and expiratory pressure gradients or the inspiratory or expiratory volume are preferably suitable measured variables, which represent indicators for the transports of breathing gases into or out of the lungs of a patient. In a preferred embodiment, the indicator for a ventilation-related shifting of secretion is calculated with the measuring, signal processing and calculating means from an inspiratory value of the quantity of gas flowing during inspiration and an expiratory value of the quantity of gas flowing during the inspiration.

In another preferred embodiment, the indicator for a ventilation-related shifting of secretion is calculated with the measuring, signal processing and calculating means from the formation of a quotient of the quantity of gas flowing during the inspiration to the quantity of gas flowing during the expiration.

In another preferred embodiment, the indicator for a ventilation-related shifting of secretion is calculated with the measuring, signal processing and calculating means by forming a quotient from the inspiratory value of the quantity of gas flowing during inspiration, which was converted by means of a progressive mathematical relationship, and from the expiratory value of the quantity of gas flowing during expiration, which was converted by means of a progressive mathematical relationship. For example, quadratic functions, exponential functions, potential functions or other functions or assignment instructions, which bring about a progressive amplification of the expiratory and inspiratory values, may be used as mathematical relationships for converting the expiratory value and the inspiratory value. The progressive mathematical relationships are used during the determination to emphasize or amplify an impulse of the quantity of gas flowing during the inspiration and of an impulse of the quantity of gas flowing during the expiration, which impulses are caused by the ventilation of a patient and with which the shifting of secretion away from the patient and to the patient is brought about. The formation of the quotient from the impulse of the quantity of gas flowing during the inspiration and from the impulse of the quantity of gas flowing during the inspiration yields a mean overall impulse as an indicator for the ventilation-related shifting of secretion. The progressive amplification offers the advantage that the sensitivity of the indicator for a ventilation-related shifting of secretion is improved, because large flow signal amplitudes can thus be described in a mathematical manner concerning their effect on the impulse of the secretion shifting nearly comparably to the real conditions prevailing in the lungs and the bronchial tract.

In another preferred embodiment, the indicator for a ventilation-related shifting of secretion is calculated with the measuring, signal processing and calculating means by forming a quotient from a square of the inspiratory value of the quantity of gas flowing during inspiration and from a square of the expiratory value of the quantity of gas flowing during expiration. The use of the quotient from the squares of the inspiratory value and the expiratory value makes it possible to obtain a simple and transparent rule for computing, whose result can be tested, verified and validated with simple means. This leads to the advantage that the calculation is possible without special requirements on the performance capacity of the measuring, signal processing and calculating means, so that it can also be run on simple processor systems (µC), as they are common in the case of sensor systems for pressure and flow measurement, for example, as a so-called embedded system. This simple and transparent rule for computing for squaring signals shows that it is possible without complicated signal processing methods (FFT analysis, wavelet analysis, etc.) to determine an indicator for a ventilation-related shifting of secretion and hence an indicator for a quality of ventilation settings.

In another preferred embodiment, the indicator for a ventilation-related shifting of secretion is calculated with the measuring, signal processing and calculating means by forming a quotient from a time integral of a square of the flow rate flowing during inspiration (inspiratory volume flow $\dot{v}_{insp}$) and from a time integral of a square of the flow rate flowing during expiration (expiratory volume flow $\dot{v}_{exsp}$). A respiratory minute volume of the patient is usually determined, as well as the balance of the inspiratory volume and the expiratory volume is usually set up when detecting and analyzing flow signals in the field of clinical medicine.

The volumes are determined via) time integrals of the flow rates flowing during inspiration and expiration. The determination of the indicator for a ventilation-related shifting of secretion by forming a quotient from the time integrals of the squares of the flow rates flowing during inspiration and expiration can be performed without complicated signal processing and measuring methods almost with or in the same measurement with the determination of the inspiratory and expiratory volumes. This type of determination of the indicator for a ventilation-related shifting of secretion by forming a quotient from the time integrals of the squares of the flow rates flowing during inspiration and expiration can thus advantageously also be included in usual systems of detecting and analyzing flow signals and volumes without a major design effort.

In another preferred embodiment, the indicator for a ventilation-related shifting of secretion is calculated with the measuring, signal processing and calculating means by forming a quotient from a time integral of a square of a flow rate flowing during inspiration, which is detected by means of an inspiratory flow sensor (inspiratory volume flow $\dot{v}_{insp}$) and from a time integral of a square of a flow rate flowing during expiration, which is detected by means of an expiratory flow sensor ($\dot{v}_{exsp}$).

In another preferred embodiment, the indicator for a ventilation-related shifting of secretion is calculated with the measuring, signal processing and calculating means by forming a quotient from a time integral of a square of a flow rate flowing during inspiration, which is detected by means of an inspiratory flow sensor (inspiratory volume flow $\dot{v}_{insp}$) and from a time integral of a square of a flow rate flowing during expiration (expiratory flow $\dot{v}_{exsp}$).

Formula 1 below shows a mathematical relationship in a general form with proportionality factors $k_1$, $k_2$ as well as scaling functions $f_1$, $f_2$ for the determination of the indicator for a ventilation-related shifting of secretion as a secretion index value ($S_i$) (mucus index) on the basis of a quotient formation from the time integral of an inspiratory measured variable $M_{insp.}$ and from the time integral of an expiratory measured variable $M_{exsp.}$.

$$S_i \approx \frac{k_1 \cdot \int [f_1(M_{insp.})]}{k_2 \cdot \int [f_2(M_{exsp.})]} \quad \text{Formula 1}$$

Formula 2 below shows as a basic formula the determination of the indicator $S_i$ with squaring of the inspiratory and expiratory flow rates as scaling factors $f_1$, $f_2$ for a ventilation-related shifting of secretion with the use of the flow rates detected as volume flows during inspiration and expiration.

$$S_i \approx \frac{k_1 \cdot \int (\dot{v}_{insp.}^2)}{k_2 \cdot \int (\dot{v}_{exsp.}^2)} \quad \text{Formula 2}$$

With $k_1=1$ and $k_2=1$, Formula 3 is obtained from Formula 2 as a simplified relationship for determining the indicator $S_i$ for a ventilation-related shifting of secretion.

$$S_i \approx \frac{\int (\dot{v}_{insp.}^2)}{\int (\dot{v}_{exsp.}^2)} \quad \text{Formula 3}$$

The integral formation is performed in Formulas 1 through 3 for integration intervals of at least one inspiration phase and at least one expiration phase, an equal number of breathing phases each being used for the inspiratory and expiratory integration intervals.

A ventilator with a ventilation system and with the medical measuring device according to the present invention represents another embodiment according to the present invention of a device, with which a shifting of secretion into the lungs of a patient can be kept as low as possible.

Such a ventilation system comprises the components actuator mechanism, sensor system, a control unit for operating a ventilation system and/or for controlling and/or regulating ventilation, inputting, outputting and transmission means for operating the ventilation system or the ventilator by a user and/or for data exchange with other devices or systems, and connection means for a pneumatic, gas-carrying connection of the ventilation system or of the ventilator to a patient. The inputting, outputting and transmission means may also comprise inputting or operating means, such as start/stop of ventilation, means for selecting and/or activating ventilation modes, means for inputting configurations, especially also for patient-specific configurations of the ventilator, besides elements for inputs or operations of the medical means in the sense of the present invention. The inputting, outputting and transmission are also especially preferably designed as a part or a module of the control unit. Elements of the medical measuring means, for example, the measuring, signal processing and calculating means, may also preferably be integrated in the control unit or connected to or coupled with same. The pneumatic or gas-carrying connection to the patient is preferably established via a ventilation tube system, wherein the ventilation tube system may be designed as a so-called two-tube system with an inspiratory feed line leading to the patient and with an expiratory discharge line away from the patient or as a so-called single-tube system, with only one inspiratory feed line to the patient.

The collective term actuator mechanism is defined in the sense of the present invention as any components for metering gases or liquids, valves, for example, metering valves, especially inspiratory metering valves and expiration valves, nonreturn valves, safety valves, as well as components for generating gas pressures, quantities of gas or gas flow rates, for example, pressure sources or ventilation drives, for example, reciprocating pumps, bellows drives, turbine drives or rotary or radial compressors (blowers), as well as side channel blowers. A ventilator or a ventilator perfected from a ventilation system and a medical measuring device is defined in the sense of the present invention, on the one hand, as ventilators for use in a clinical environment in the emergency admission unit, for use in diagnostic units, for use on patient wards and for use during transportation within hospitals, intensive care ventilators for use in an intensive care unit, emergency ventilators for mobile use in emergency and transportation situations, and, on the other hand, also as anesthesia apparatuses for use during a surgery or in the induction room or the recovery room.

In a preferred embodiment of the ventilator, the measuring, signal processing and calculating unit or the control unit is designed to compare the indicator for the ventilation-related shifting of secretion with a defined value.

In another embodiment of the ventilator, the inputting, outputting and transmission means are designed to transmit the indicator for the ventilation-related shifting of secretion, a result of the comparison of the indicator for the ventilation-related shifting of secretion with a defined value or an indication concerning a relation of the indicator for the ventilation-related shifting of secretion to the defined value and to output these to a user.

Further, provisions may also be made in or at the ventilator for the control unit or the inputting, outputting and transmission unit to be designed to output an indication for adapting one or more ventilation parameters, an indication for the selected ventilation mode in relation to the ventilation-related shifting of secretion or an indication for adapting one or more ventilation parameters with at least one suggested value for the at least one ventilation parameter or the ventilation mode.

In a variant of this other preferred embodiment, the ventilator with the inputting, outputting and transmission unit and with the control unit is designed to request a confirmation for the at least one suggested value, to receive the confirmation as an input and to use the suggested value for a further operation of the ventilator.

In another embodiment of the ventilator, the control unit and the actuator mechanism are designed to change or adapt a set value of an inspiratory pressure in case of a deviation of the indicator of the ventilation-related shifting of secretion from a defined value, to change or adapt a set value of an inspiratory flow rate or a maximum of an inspiratory flow rate, to change or adapt a rise of a pressure ramp of the inspiratory pressure, to change or adapt a rise time of the pressure ramp of the inspiratory pressure, and to change or adapt an inspiration to expiration ratio, an inspiratory pause during the inspiration phase or a respiration rate.

In another preferred variant of the other embodiment of the ventilator, the set value of the inspiratory pressure is reduced by the control unit interacting with the actuator mechanism in case the indicator of the ventilation-related shifting of secretion exceeds the defined value.

In another preferred variant of the other embodiment of the ventilator, the set value of the inspiratory pressure is increased by the control unit interacting with the actuator mechanism in case the indicator of the ventilation-related shifting of secretion is below the defined value.

In another preferred variant of the other embodiment of the ventilator, the set value of the inspiratory flow rate is reduced by the control unit interacting with the actuator mechanism in case the indicator of the ventilation-related shifting of secretion exceeds the defined value. In another preferred variant of the other embodiment of the ventilator, the set value of the inspiratory flow rate is increased by the control unit interacting with the actuator mechanism in case the indicator of the ventilation-related shifting of secretion is below the defined value.

In another preferred variant of the other embodiment of the ventilator, the maximum of the inspiratory flow rate is limited by the control unit interacting with the actuator mechanism in case the indicator of the ventilation-related shifting of secretion exceeds the defined value. In another preferred variant of the other embodiment of the ventilator, the limitation of the maximum of the inspiratory flow rate is eliminated by the control unit interacting with the actuator mechanism in case the indicator of the ventilation-related shifting of secretion is below the defined value.

The limitation of the maximum of the inspiratory flow rate, as well as the elimination of the limitation of the maximum of the inspiratory flow rate are performed stepwise in a special embodiment.

In another embodiment, the limitation of the maximum of the inspiratory flow rate is performed in relation to the maximum of the expiratory flow rate. Formula 4 shows the relationship between the maxima of the inspiratory flow rate ($\dot{v}_{max\_insp.}$) and the expiratory flow rate ($\dot{v}_{max\_exsp.}$):

$$\dot{v}_{max\_insp.} \approx k_3 \cdot \dot{v}_{max\_exsp.} \qquad \text{Formula 4}$$

k3 is preferably selected here in a range of 0.45 to 0.95, so that it is ensured that the maximum of the expiratory flow rate is greater than the maximum of the inspiratory flow rate. The advantages and the effect of a limitation of the maximum of the inspiratory flow rate are seen in Formula 3. The secretion index value ($S_i$) (mucus index) is reduced by inspiratory flow rates with a high percentage of secretion shifting index being reduced.

In another preferred variant of the other embodiment of the ventilator, the rise of the pressure ramp of the inspiratory pressure is reduced by the control unit interacting with the actuator mechanism in case the indicator of the ventilation-related shifting of secretion exceeds the defined value. In another preferred variant of the other embodiment of the ventilator, the duration of the rise time of the pressure ramp of the inspiratory pressure is increased by the control unit interacting with the actuator mechanism in case the indicator of the ventilation-related shifting of secretion is below the defined value.

In another preferred variant of the other embodiment of the ventilator, the duration of the rise time of the pressure ramp of the inspiratory pressure is increased by the control unit interacting with the actuator mechanism in case the indicator of the ventilation-related shifting of secretion exceeds the defined value. In another preferred variant of the other embodiment of the ventilator, the duration of the rise time of the pressure ramp of the inspiratory pressure is reduced by the control unit interacting with the actuator mechanism in case the indicator of the ventilation-related shifting of mucus is below the defined value.

In another preferred variant of the other embodiment of the ventilator, an inspiratory pause is prolonged by the control unit interacting with the actuator mechanism in case the indicator of the ventilation-related shifting of secretion during the inspiration phase exceeds the defined value. In another preferred variant of the other embodiment of the ventilator, the duration of the inspiratory pause is reduced by the control unit interacting with the actuator mechanism in case the indicator of the ventilation-related shifting of secretion during the inspiration phase is below the defined value.

In another embodiment of the ventilator, the control unit and the actuator mechanism are designed such that they interact with one another to reduce a set value of an inspiratory pressure, to reduce a rise of a pressure ramp of the inspiratory pressure or to increase the duration of the rise time of the pressure ramp of the inspiratory pressure in case the indicator of the ventilation-related shifting of secretion exceeds the defined value, so that the indicator of the ventilation-related shifting of secretion will again drop below the defined value as a result.

The control unit and the actuator mechanism are, furthermore, designed preferably such that they interact in this other embodiment of the ventilator to increase the set value of the inspiratory pressure, to increase the rise of the pressure ramp of the inspiratory pressure or to reduce the duration of the rise time of the pressure ramp of the inspiratory pressure in case the indicator of the ventilation-related shifting of secretion is below the defined value, so that the indicator of the ventilation-related shifting of secretion will again exceed the defined value as a result.

In another embodiment of the ventilator, the control unit and the actuator mechanism are designed such that they interact to change or adapt an inspiration to expiration ratio and/or a respiration rate and/or an inspiratory pause during the inspiration phase in case the indicator of the ventilation-related shifting of secretion exceeds the defined value, so that the indicator of the ventilation-related shifting of secretion will again drop below the defined value as a result. The control unit and the actuator mechanism are, furthermore, designed such that they cooperate in this other embodiment of the ventilator to change or adapt the inspiration to expiration ratio and/or the respiration rate and/or the inspiratory pause during the inspiration phase in case the indicator of the ventilation-related shifting of secretion is below the defined value, so that the indicator of the ventilation-related shifting of secretion will again exceed the defined value as a result.

The control unit and the actuator mechanism are, furthermore, preferably designed such that they cooperate in this other embodiment of the ventilator to increase the duration of an inspiratory pause in case the indicator of the ventilation-related shifting of secretion during the inspiration phase is below the defined value, so that the indicator of the ventilation-related shifting of secretion will again exceed the defined value as a result.

In another embodiment of the ventilator, the maximum of the inspiratory flow rate is limited stepwise by the control unit interacting with the actuator mechanism in case the indicator of the ventilation-related shifting of secretion exceeds the defined value until the indicator of the ventilation-related shifting of secretion drops again below the defined value.

In this other embodiment of the ventilator, the limitation of the maximum of the inspiratory flow rate is eliminated stepwise by the control unit interacting with the actuator mechanism in case the indicator of the ventilation-related shifting of secretion is below the defined value until the indicator of the ventilation-related shifting of secretion again exceeds the defined value.

A method according to the present invention for operating a medical measuring device or a method according to the present invention for operating a ventilator with reduced shifting of secretion into the lungs is designed by a sequence of steps with a plurality of steps or partial steps.

To carry out the method according to the present invention with reduced shifting of secretion into the lungs, the ventilator is preferably designed as a ventilator and anesthesia apparatus, wherein at least one operating and control module is preferably provided in the ventilator and anesthesia apparatus to control and to operate the ventilator and anesthesia apparatus.

It is, further, preferred to execute the sequence of steps by at least one operating and control module. The operating and control module may also be provided partly or as a whole as a computer program or as a computer program product.

It is therefore recognized that the scope of protection of the present application may likewise cover the computer program product and the computer program.

The operating and control module preferably comprises the measuring, signal processing and calculating means, the control unit, as well as preferably data storage means and inputting, outputting and transmission means.

In a first step, an inspiratory measured variable and an expiratory measured variable are detected by means of the sensor system and with the measuring, signal processing and calculating means in the method according to the present invention for operating a medical measuring device or for operating a ventilator, in a second step, the inspiratory measured variable is converted mathematically with the measuring, signal processing and calculating means into an inspiratory impulse parameter by means of a first progressive mathematical relationship, and the expiratory measured variable is mathematically converted into an expiratory impulse parameter by means of a second progressive mathematical relationship, in a third step, a quotient is formed with the measuring, signal processing and calculating means from the inspiratory impulse parameter and the expiratory impulse parameter as an indicator of a ventilation-related shifting of secretion.

In a preferred embodiment of the method, the indicator for the ventilation-related shifting of secretion is outputted or transmitted in a further step with the inputting, outputting and transmission means.

In another preferred embodiment of the method, the indicator for the ventilation-related shifting of secretion is compared in a further step with a defined value with the measuring, signal processing and calculating means, and an indication concerning a relation of the indicator of the ventilation-related shifting of secretion to the defined value is transmitted or outputted to a user by means of the inputting, outputting and transmission means. In a special variant of this other preferred embodiment, an indication for adapting one or more ventilation parameters, an indication for the selected ventilation mode in relation to the ventilation-related shifting of secretion, or an indication for adapting one or more ventilation parameters with at least one suggested value for the at least one ventilation parameter or the ventilation mode is outputted in this additional step with the inputting, outputting and transmission means.

In a subsequent, further step, a confirmation is requested for the at least one suggested value by means of the control unit in conjunction with the inputting, outputting and transmission means in this special variant of this other preferred embodiment, and this suggested value is used by the control unit for a further operation of the ventilator in a subsequent, further step after receiving the confirmation at the inputting, outputting and transmission unit.

In another embodiment of the method, the indicator for the ventilation-related shifting of secretion is compared with a defined value in a further step with the measuring, signal processing and calculating means, and an inspiratory pressure is changed or adapted, a set value or a maximum of an inspiratory flow is changed or adapted, a rise of a pressure ramp of an inspiratory pressure is changed or adapted, or the duration of a rise time of the pressure ramp of the inspiratory pressure is changed or adapted in case of a deviation of the indicator for the ventilation-related shifting of secretion from the defined value.

In another preferred variant of the other embodiment of the method, the set value of the inspiratory pressure is reduced in a further step in case the indicator of the ventilation-related shifting of secretion exceeds the defined value. In another preferred variant of the other embodiment of the method, the set value of the inspiratory pressure is increased in a further step in case the indicator of the ventilation-related shifting of secretion is below the defined value.

In another preferred variant of the other embodiment of the method, the rise of the pressure ramp of the inspiratory pressure is reduced in a further step in case the indicator of the ventilation-related shifting of secretion exceeds the defined value.

In another preferred variant of the other embodiment of the method, the rise of the pressure ramp of the inspiratory pressure is increased in case the indicator of the ventilation-related shifting of secretion is below the defined value.

In another preferred variant of the other embodiment of the method, the duration of the rise time of the pressure ramp of the inspiratory pressure is increased in a further step in case the indicator of the ventilation-related shifting of secretion exceeds the defined value. In another preferred variant of the other embodiment of the method, the duration of the rise time of the pressure ramp of the inspiratory pressure is reduced in case the indicator of the ventilation-related shifting of secretion is below the defined value.

In another preferred embodiment of the method, the indicator for the ventilation-related shifting of secretion is compared with a defined value in a further step with the measuring, signal processing and calculating means, and a set value of an inspiratory pressure is reduced, a rise of the pressure ramp of the inspiratory pressure is reduced, a set value of an inspiration flow is reduced, a maximum of the inspiration flow is limited or the duration of the rise time of the pressure ramp of the inspiratory pressure is increased by means of the control unit and the actuator mechanism in case the defined value is exceeded, so that the indicator of the ventilation-related shifting of secretion will again be below the defined value as a result.

In another preferred embodiment of the method, the indicator of the ventilation-related shifting of secretion is compared with a defined value in a further step with the measuring, signal processing and calculating means, and an inspiration to expiration ratio and/or a respiration rate is changed by means of the control unit and the actuator mechanism in case the defined value is exceeded such that the indicator of the ventilation-related shifting of secretion will again be below the defined value as result.

The above-described embodiments of the method according to the present invention may also be designed as a computer program product with a computer program, and a computer is prompted to execute the above-described method according to the present invention when the computer program is executed on the computer or on a processor of the computer. An alternative means of accomplishing the object is a computer program with computer program code for executing all steps of the method being claimed or of the above-described method when the computer program is executed on the computer. The computer program may also be stored on a machine-readable storage medium. An alternative means of accomplishing the object makes provisions for a storage medium, which is intended for the storage of the above-described, computer-implemented method and is readable by a computer. It is within the scope of the present invention that not all steps of the method necessarily have to be executed on one and the same computer, but they may also be executed on different computers. The sequence of the steps of the method may optionally be varied as well. Moreover, it is possible that individual sections of the above-described method may be executed in a commercially available unit (e.g., the inputting, outputting and transmission unit) and the remaining components in another commercially available unit (e.g., the medical measuring device, the operating and control module or the device per se), quasi as a distributed system.

The means of accomplishing the object was described above with respect to the method being claimed. Features, advantages or alternative embodiments mentioned here can also be applied to the other objects of the medical measuring device or of the ventilator and vice versa. In other words, the object-related claims (which are directed, for example, towards a module or a device), may also be perfected with the features that are described or claimed in connection with the method. The corresponding functional features of the method are designed by corresponding object-related modules, especially by hardware components, which may be implemented, for example, in the form of a microprocessor (μP), microcontroller (μC) or in the form of instructions, which are stored in an electronic circuit in a memory component and are processed by a processor.

A use according to the present invention of the medical measuring device is designed by a confirmation being requested with the inputting, outputting and transmission means for the at least one suggested value, by a confirmation-specific signal being detected, by the confirmation-specific signal being processed into a control signal, and by the control signal being made available at a control unit of a ventilator.

The present invention will be explained in more detail below on the basis of figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
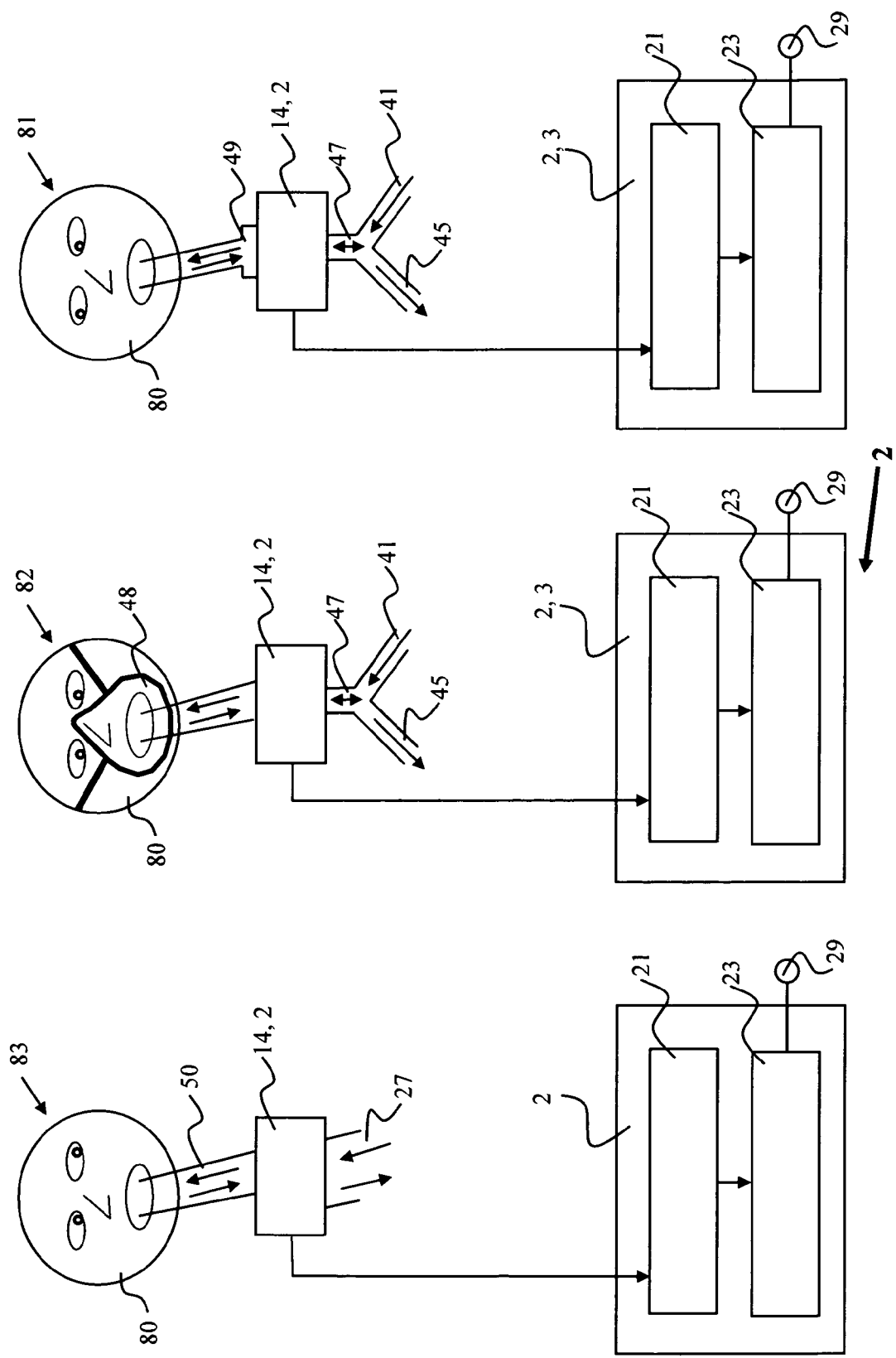
FIG. 1 is a schematic view showing a medical measuring device.

FIG. 1 shows a medical measuring device 2 connected to a patient 80, which illustrates three different possibilities of connecting the medical measuring device 2 to the patient 80 in three graphic variants 81, 82, 83. In the first graphic variant 81, the patient 80 is supplied with breathing gas via an endotracheal tube 49. The patient 80 is supplied with breathing gas via a nasal mask 48 in the second graphic variant 82. Both the nasal mask 48 and the endotracheal tube 49 are connected pneumatically to an inspiratory and expiratory flow sensor 14. A ventilator, emergency ventilator or anesthesia apparatus, not shown in this FIG. 1, is connected to the inspiratory and expiratory flow sensor 14 by means of a connection piece 47, a so-called Y-piece 47, of an expiratory ventilation tube 45 and an inspiratory ventilation tube 41. In a special variant, the inspiratory and expiratory flow sensor 14 may be designed such that it is coupled in or on the connection piece 47 or is integrated in this connection piece 47. The connection of a patient 80 to a ventilator is provided and is necessary for the ventilation a patient 80. In the third graphic variant 83, the patient 80 is connected to the medical measuring device 2 in a gas-carrying manner via a mouthpiece 50, without there being a connection to the ventilator. The patient inhales breathing air freely from a surrounding area 27 and exhales it freely into the surrounding area 27 through the mouthpiece 50 and the inspiratory and expiratory flow sensor 14. The medical measuring device 2 has a measuring, signal processing and calculating unit 21 with measuring, signal processing and calculating means and with calculating means and an inputting, outputting and transmission unit 23 with inputting means, for example, key and switching elements, touch-sensitive screen keyboards, outputting means, for example, illuminants, optical and/or acoustic signal means, screens, and transmission means, for example, wired or wireless interfaces. The measuring, signal processing and calculating unit 21 and the inputting, outputting and transmission unit 23 are designed together as a central operating and control module 3 in this embodiment according to FIG. 1. The inspiratory and expiratory flow sensor 14 and the central operating and control module 3 thus form together essentially the medical measuring device 2 in this FIG. 1. An interface 29 for exchanging data with external devices (screens, ventilators, monitoring systems) or networks, not sown in this FIG. 1, are provided at the inputting, outputting and transmission unit 23. This interface 29 may be designed as a wired interface, for example, as a data network, LAN, Ethernet, VGA, DVI, HDMI, USB, RS232, RS485, TOS-Link, or as a wireless interface, for example, as a radio network, WLAN, IrDA, IrOBEX. The inspiratory and expiratory flow sensor 14 is connected to the measuring, signal processing and calculating unit 21 for data and signal technology, and an inspiratory flow rate and an expiratory flow rate, which are detected with the inspiratory and expiratory flow sensor 14 in the measuring, signal processing and calculating unit 21 are converted by means of a calculation based on one of the Formulas 2 or 3 into the indicator $S_i$ for a ventilation-related shifting of secretion. This indicator $S_i$ is transmitted by the measuring, signal processing and calculating unit 21 to the inputting, outputting and transmission unit 23, and classification of the indicator into a defined value range may also be performed in the measuring, signal processing and calculating unit 21, e.g., by means of a threshold value comparison. The indicator $S_i$ is outputted directly with adapted color to the user and/or is made available at the interface 29 by means of the inputting, outputting and transmission unit 23, for example, numerically, graphically or in a processed form, for example, in relation to a threshold value.

Figure 2:
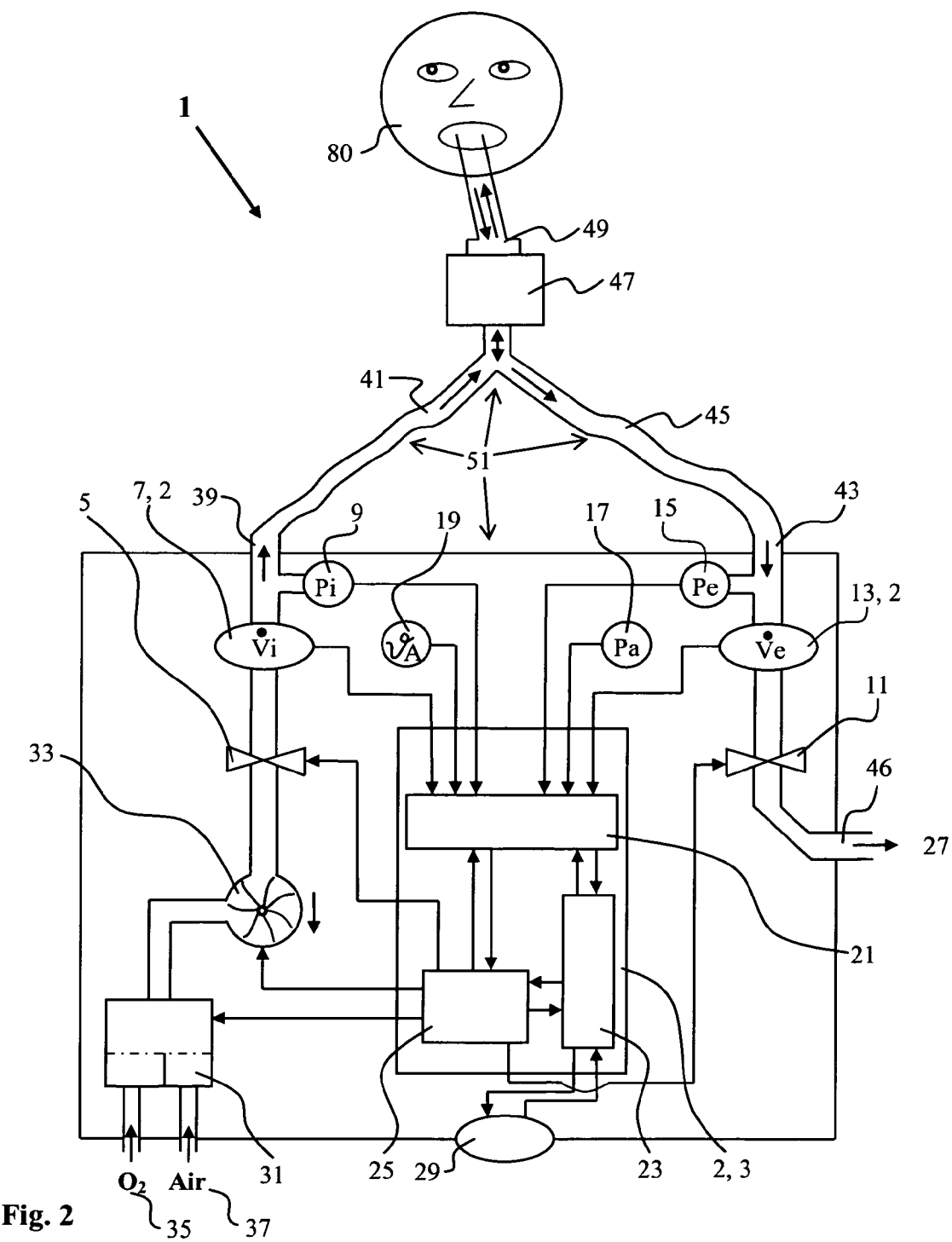
FIG. 2 is a schematic view showing a ventilator.

FIG. 2 shows a ventilator 1 connected to a patient 80 as a variant of a perfection of the medical measuring device 2 according to FIG. 1. Identical elements in FIGS. 1 and 2 are designated by the same reference numbers in FIG. 2. There is a central operating and control module 3 in this FIG. 3, which module comprises a measuring, signal processing and calculating unit 21 with measuring, signal processing and calculating means and with measuring means, signal processing means and calculating means, an inputting, outputting and transmission unit 23 with inputting means, for example, key and switching elements, touch-sensitive screens, keyboards, outputting means, for example, illuminants, optical and/or acoustic signal means, and a data interface 29 and a control unit 25 for controlling and/or regulation. The ventilator 1 has an inspiratory gas outlet 39 and an expiratory gas inlet 43. The patient 80 is connected to the expiratory gas inlet 43 via an endotracheal tube 49 in a gas-carrying manner by means of a connection piece 47 via an expiratory ventilation tube 45, and to the inspiratory gas outlet 39 via an inspiratory ventilation tube 41. Furthermore, the ventilator 1 has an inspiratory flow sensor 7 and an inspiratory pressure sensor 9 at the inspiratory gas outlet 39, as well as an expiratory flow sensor 13 and an expiratory pressure sensor 15 at the expiratory gas inlet 43. Additional sensors are an ambient pressure sensor 17 and an ambient temperature sensor 19. The sensors 7, 9, 13, 15, 17, 19 are connected to the operating and control module 3 for data and signal technology. The measuring, signal processing and calculating unit 21, the inputting, outputting and transmission unit 23 and the interface 29 have comparable designs and are provided with comparable functionalities, as described in connection with FIG. 1. The control unit 25 is additionally also arranged in the central operating and control module 3 in order to control and/or regulate and thus carry out the operation of the ventilator 1 for ventilating a patient 80 by means of an inspiratory metering valve 5 arranged in the inspiratory gas outlet 39 and connected to the control unit 25 for data and signal technology and by means of an expiration valve 11 arranged in the expiratory gas inlet 43 and connected to the control unit 25 for data and signal technology. Additional components in the ventilator 1 for performing the ventilation are a gas-mixing unit 31 and a ventilation drive 33. By means of a valve and sensor system arrangement, not shown in this FIG. 2, the gas-mixing unit 31 mixes gases and/or fluids, which are fed to the gas-mixing unit 31 via a first gas port 35, for example, as pressurized oxygen, and via a second gas port 37, for example, as medical pressurized air oxygen, and makes these available as fresh breathing gas for the ventilation drive 33. The ventilation drive 33 is preferably designed, for example, as a bellows drive or as a radial blower. The fresh breathing gas flows from the ventilation drive 33 during inhalation (inspiration) into the lungs of a patient 80 through the inspiration metering 5 actuated by the control unit 25 through the inspiration flow sensor 7 via the inspiratory gas outlet 39 and via an inspiratory ventilation tube 41, the connection piece 47 by means of an endotracheal tube 49 or, as an alternative, by means of a nasal mask 48, not shown in this FIG. 2. Consumed breathing gas flows from the patient 80 through the endotracheal tube 49 or the nasal mask 48 during exhalation (expiration) back to the expiratory gas inlet 43 into the ventilator 1 via the connection piece 47 and an expiratory ventilation tube 45, and finally to a surrounding area 27 outside the ventilator 1 via a waste air outlet 46 through the expiratory flow sensor 13 and through the expiration valve 11 actuated by the control unit 25. The connection piece 47, the endotracheal tube 49, the inspiratory ventilation tube 41, and the expiratory ventilation tube 45 form a so-called ventilation system 51 with the sensor system 7, 9, 13, 15, 17, 19, the gas-mixing unit 31, the ventilation drive 33, the expiration valve 11, the inspiration metering valve 5 and the control unit 25.

Together with the medical measuring device 2 (FIG. 1), the ventilation system 51 forms the ventilator 1. The medical measuring device 2 (FIG. 1) is incorporated in a central operating and control module 3 in this FIG. 2. The inspiratory flow sensor 7 and the expiratory flow sensor 13 are connected to the measuring, signal processing and calculating unit 21 for data and signal technology, an inspiratory flow rate, detected with the inspiratory flow sensor 7, and an expiratory flow rate, detected with the expiratory flow sensor 13, are converted into the indicator $S_i$ for a ventilation-related shifting of secretion by means of one of Formulas 2 or Formula 3. This indicator $S_i$ is transmitted by the signal processing and calculating unit 21 to the inputting, outputting and transmission unit 23, and a classification of the indicator into a defined value range may also be performed in the measuring, signal processing and calculating unit 21, e.g., by means of a threshold value comparison. By means of the inputting, outputting and transmission unit 23, the indicator $S_i$ is outputted to the user and/or made available at the interface directly, for example, numerically, graphically or in a processed form, for example, in relation to a threshold value, in an adapted color. Furthermore, the indicator $S_i$ may be transmitted to the control unit 25 directly or in a processed or converted form. The control unit 25 is designed to adapt the ventilation drive 33 of the ventilator 1 for ventilating a patient 80 on the basis of the indicator $S_i$.

An adaptation on the basis of the indicator $S_i$ may be performed by varying an inspiratory pressure, by varying a rise of the pressure ramp of the inspiratory pressure or the duration of a rise time of the pressure ramp of the inspiratory pressure, by varying the inspiratory flow rate, by limiting a maximum of the inspiratory flow rate, by varying an inspiratory pause, by changing a respiration rate or by changing an I:E ratio.

Figure 3:
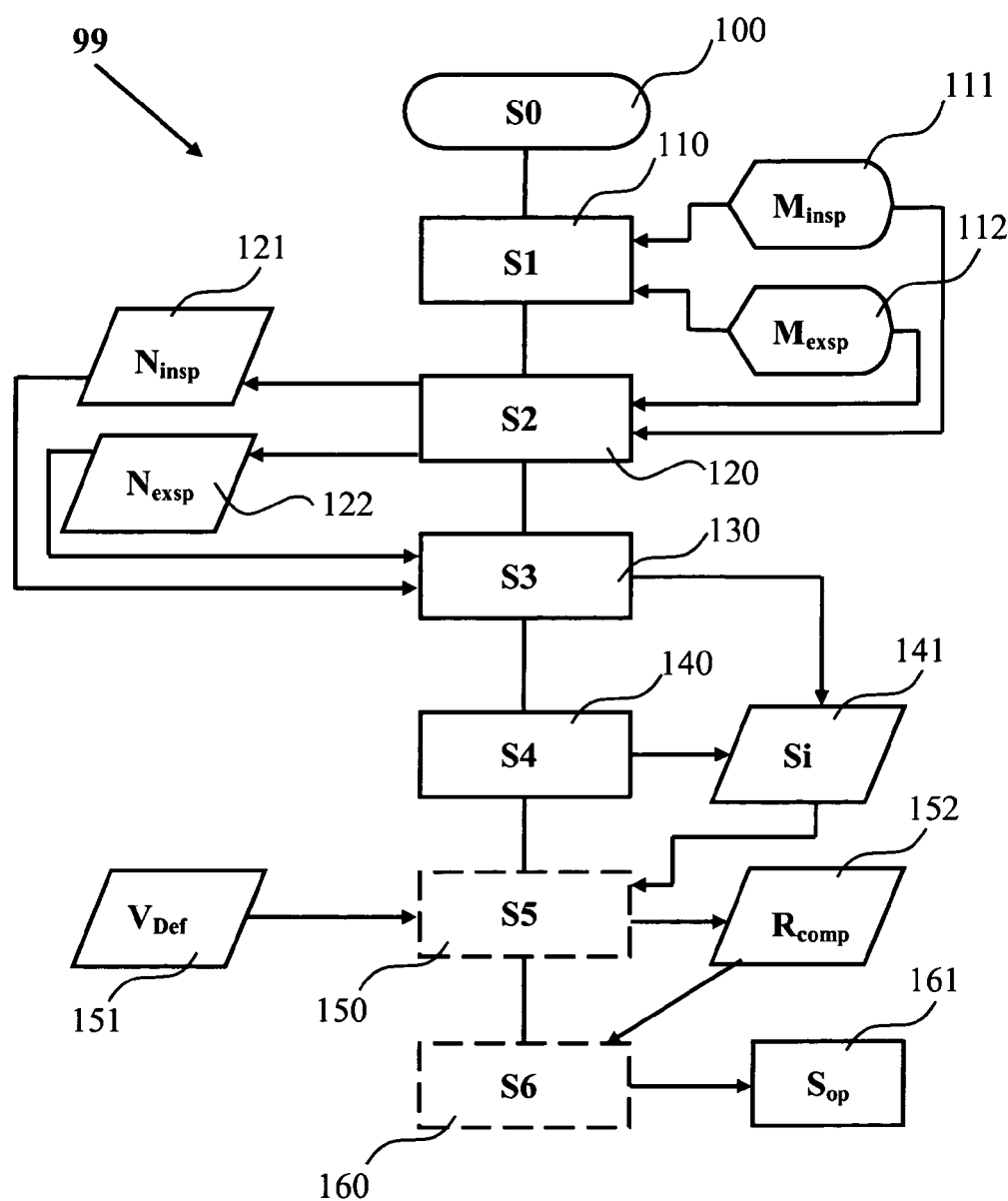
FIG. 3 is a flow chart showing a method for operating a medical measuring device.

FIG. 3 shows a schematic flow chart 99 of a method for operating a medical measuring device 2 (FIG. 1) with an inspiratory and expiratory flow measurement, for example, for operating the medical measuring device 2 according to FIG. 1 or for operating the ventilator 1 according to FIG. 2.

After a start S0 100 of the medical measuring device 2, an inspiratory measured value $M_{insp.}$ 111 and an expiratory measured value $M_{exsp.}$ 112 are detected in a first step S1 110.

In a second step S2 120, the inspiratory measured value $M_{111}$ 111 is converted by means of a mathematical relationship and integral formation over an integration interval of one inspiration phase into the inspiratory impulse parameters 121, and the expiratory measured value $M_{exsp.}$ 112 is converted into an expiratory impulse parameter $N_{exsp.}$ 122 by means of a mathematical relationship and integral formation over an integration interval of one expiration phase.

In a third step S3 130, a quotient is formed from the inspiratory impulse parameters $N_{insp.}$ 121 and the expiratory impulse parameters $N_{exsp.}$ 122 and the indicator $S_i$ for a ventilation-related shifting of secretion 141 is thus determined.

In a fourth step S4 140, the indicator $S_i$ 141 for a ventilation-related shifting of secretion is outputted or made available.

In an optimal fifth step S5 150, the indicator $S_i$ 141 is compared with a defined value $V_{Def}$ 151 and outputted as a result $R_{comp}$ 152. The result $R_{comp}$ 152 of the comparison is used in another optimal sixth step S6 160 in order to set an operating state $S_{op}$ 161 of the ventilator 1 (FIG. 2) adapted to the indicator $S_i$ 141, to the defined value $V_{Def}$ 151 or to the difference between the defined value $V_{Def}$ 151 and the indicator $S_i$ 141.

While specific embodiments of the invention have been shown and described in detail to illustrate the application of the principles of the invention, it will be understood that the invention may be embodied otherwise without departing from such principles.

The invention claimed is:

1. A medical measuring device comprising:
   a sensor system configured to detect an inspiratory measured variable, which represents an indicator for the transport of breathing gases into the lungs of a patient, and configured to detect an expiratory measured variable, which represents an indicator for the transport of breathing gases from the lungs of a patient; and
   a measuring, signal processing and calculating device configured to determine an indicator for a ventilation-related shifting of secretion from a quotient of the inspiratory measured variable and the expiratory measured variable.

2. A medical measuring device in accordance with claim 1, wherein the sensor system for detecting the inspiratory measured variable is an inspiratory flow sensor or an inspiratory pressure sensor.

3. A medical measuring device in accordance with claim 1, wherein the sensor system for detecting the expiratory measured variable is an expiratory flow sensor or an expiratory pressure sensor.

4. A medical measuring device in accordance with claim 1, wherein the sensor system for detecting the inspiratory measured variable and for detecting the expiratory measured variable is an inspiratory and expiratory flow sensor or an inspiratory and expiratory flow sensor located close to the patient.

5. A medical measuring device in accordance with claim 1, wherein the measuring, signal processing and calculating device is configured to carry out a comparison of the indicator for the ventilation-related shifting of secretion with a defined value.

6. A medical measuring device in accordance with claim 5, further comprising:
   an inputting, outputting and transmission device, wherein the inputting, outputting and transmission device is configured to output, display or transmit the indicator for a ventilation-related shifting of secretion, a result of the comparison between the indicator for the ventilation-related shifting of secretion and a defined value or an indication concerning a relation of the indicator for the ventilation-related shifting to the defined value.

7. A ventilator comprising:
a ventilation system;
an actuator mechanism, for transporting breathing gases into the lungs of a patient and out of the lungs of a patient, arranged in or at the ventilation system
a control unit controlling an operation of the ventilation system and at least one of controlling and regulating ventilation, the control unit being arranged in or at the ventilation system;
an inputting, outputting and transmission device at least one of operating the ventilation system or the ventilator and exchanging data with other devices or systems, the inputting, outputting and transmission device being arranged in or at the ventilation system; and
connection means for the pneumatic, gas-carrying connection of the ventilation system to a patient arranged in or at the ventilation system; and
a medical measuring device comprising:
a sensor system configured to detect an inspiratory measured variable, which represents an indicator for the transport of breathing gases into the lungs of a patient, and configured to detect an expiratory measured variable, which represents an indicator for the transport of breathing gases from the lungs of a patient; and
a measuring, signal processing and calculating device configured to determine an indicator for a ventilation-related shifting of secretion from a quotient of the inspiratory measured variable and the expiratory measured variable.

8. A ventilator in accordance with claim 7, wherein the control unit is configured to change or adapt a set value of an inspiratory pressure, to change or adapt a set value of an inspiratory flow rate, to change or adapt a maximum of an inspiratory flow rate, to change or adapt a rise of a pressure ramp of the inspiratory pressure, to change or adapt the duration of a rise time of the pressure ramp of the inspiratory pressure, to change or adapt an inspiratory pause, and to change or adapt an inspiration to expiration ratio or a respiration rate in case the indicator of the ventilation-related shifting of secretion deviates from the defined value.

9. A ventilator in accordance with claim 7, wherein the control unit, interacting with the actuator mechanism, is configured to reduce a set value of an inspiratory pressure, to reduce a set value of an inspiration flow rate, to limit a maximum of an inspiration flow rate, to reduce a rise of a pressure ramp of the inspiratory pressure or to increase the duration of a rise time of the pressure ramp of the inspiratory pressure or to increase the duration of an inspiratory pause in case the indicator of the ventilation-related shifting of secretion exceeds the defined value, so that the indicator of the ventilation-related shifting of secretion will again drop below the defined value as a result.

10. A ventilator in accordance with claim 7, wherein the control unit, interacting with the actuator mechanism, is configured at least one of to change or adapt an inspiration to expiration ratio and a respiration rate in case the indicator of the ventilation-related shifting of secretion exceeds the defined value, so that the indicator of the ventilation-related shifting of secretion will again drop below the defined value as a result.

11. A ventilator in accordance with claim 7, wherein the measuring, signal processing and calculating device or the control unit are designed to compare the indicator for the ventilation-related shifting of secretion with a defined value.

12. A ventilator in accordance with claim 11, wherein the inputting, outputting and transmission device is configured to transmit the indicator for the ventilation-related shifting of secretion, a result of the comparison between the indicator for the ventilation-related shifting of secretion and a defined value or an indication concerning a relation of the indicator of the ventilation-related shifting of secretion to the defined value or to output same at a user.

13. A method for operating a medical measuring device comprising a sensor system configured to detect an inspiratory measured variable, which represents an indicator for the transport of breathing gases into the lungs of a patient, and configured to detect an expiratory measured variable, which represents an indicator for the transport of breathing gases from the lungs of a patient and a measuring and a signal processing and calculating device configured to determine an indicator for a ventilation-related shifting of secretion from the expiratory measured variable and the inspiratory measured variable, the method comprising the steps of:
detecting an inspiratory measured variable and an expiratory measured variable are detected in a first step by means of with the sensor system;
with the measuring, signal processing and calculating device in a second step, converting the inspiratory measured variable mathematically into an inspiratory impulse parameter by means of a first progressive mathematical relationship, and converting the expiratory measured variable is converted mathematically into an expiratory impulse parameter by means of a second progressive mathematical relationship; and
forming a quotient, with the measuring, signal processing and calculating device, from the inspiratory impulse parameter and the expiratory impulse parameter as an indicator for a ventilation-related shifting of secretion.

14. A method in accordance with claim 13, wherein the indicator for the ventilation-related shifting of secretion is outputted or transmitted in an additional step with an inputting, outputting and transmission device.

15. A method in accordance with claim 13, wherein the indicator for the ventilation-related shifting of secretion is compared with a defined value in an additional step with the measuring, signal processing and calculating unit, and an indication concerning a relation of the indicator of the ventilation-related shifting of secretion to the defined value is transmitted or outputted to a user by means of an inputting, outputting and transmission device.

16. A method in accordance with claim 13, wherein a medical measuring device is part of a ventilator that further comprises:
a ventilation system;
an actuator mechanism, transporting breathing gases into the lungs of a patient and out of the lungs of a patient, arranged in or at the ventilation system;
a control unit controlling an operation of the ventilation system and at least one of controlling and regulating ventilation, the control unit being arranged in or at the ventilation system;
an inputting, outputting and transmission device at least one of operating the ventilation system or the ventilator and exchanging data with other devices or systems, the inputting, outputting and transmission device being arranged in or at the ventilation system; and
connection means, for a pneumatic, gas-carrying connection of the ventilation system to a patient, arranged in or at the ventilation system.

17. A method in accordance with claim 16, wherein the indicator for the ventilation-related shifting of secretion is outputted or transmitted in an additional step with the inputting, outputting and transmission device.

18. A method in accordance with claim 16, wherein the indicator for the ventilation-related shifting of secretion is compared in an additional step by means of the measuring, signal processing and calculating unit with a defined value, and an indication concerning a relation of the indicator of the ventilation-related shifting to the defined value is transmitted or outputted to a user by means of the inputting, outputting and transmission device.

19. A method in accordance with claim 16, wherein the indicator for the ventilation-related shifting of secretion is compared with a defined value in an additional step with the measuring, signal processing and calculating device, and an inspiratory pressure is changed or adapted, a set value or a maximum of an inspiration flow is changed or adapted, a rise of a pressure ramp of an inspiratory pressure is changed or adapted or the duration of a rise time of the pressure ramp of the inspiratory pressure is changed or adapted by means of the control unit and the actuator mechanism in case of a deviation of the indicator for the ventilation-related shifting of secretion from the defined value.

20. A method in accordance with claim 16, wherein the indicator for the ventilation-related shifting of secretion is compared with a defined value in an additional step with the measuring, signal processing and calculating device, and if the defined value is exceeded, a set value of an inspiratory pressure is reduced, a set value of an inspiration flow is reduced, a maximum of the inspiration flow is limited, a rise of the pressure ramp of the inspiratory pressure is reduced, or the duration of a rise time of a pressure ramp of the inspiratory pressure is increased by means of the control unit and the actuator mechanism, so that the indicator of the ventilation-related shifting of secretion will again drop below the defined value as a result.

21. A method in accordance with claim 16, wherein the indicator for the ventilation-related shifting of secretion is compared with a defined value in an additional step with the measuring, signal processing and calculating unit, and if the defined value is exceeded, an inspiration to expiration ratio and/or a respiration rate and/or an inspiratory pause is changed or adapted by means of the control unit and the actuator mechanism such that the indicator of the ventilation-related shifting of secretion will again drop below the defined value as a result.

22. A method in accordance with claim 16, wherein the indicator for the ventilation-related shifting of secretion is compared with a defined value in an additional step by means of the measuring, signal processing and calculating device, and an indication for adapting one or more ventilation parameters, an indication for the selected ventilation mode in relation to the ventilation-related shifting of secretion or an indication for adapting one or more ventilation parameters with at least one suggested value for the at least one ventilation parameter or the ventilation mode is outputted with the inputting, outputting and transmission device.

23. A method in accordance with claim 22, wherein a confirmation for the at least one suggested value is requested in a next, additional step by means of the control unit in conjunction with the inputting, outputting and transmission device, and this suggested value is used by the control unit for a further operation of the ventilator in a subsequent, additional step after receiving this confirmation at the inputting, outputting and transmission unit.

24. A method accordance with claim 22, wherein the sensor system for detecting the expiratory measured variable is an expiratory flow sensor or an expiratory pressure sensor, and further comprising the steps of:
  requesting a confirmation for the at least one suggested value;
  detecting a confirmation-specific signal;
  processing the confirmation-specific signal into a control signal; and
  making available the control signal at a control unit of a ventilator with an inputting, outputting and transmission device.

* * * * *